United States Patent [19]
Tang et al.

[11] Patent Number: 4,704,483
[45] Date of Patent: Nov. 3, 1987

[54] 3,4-DIFLUORO-5-NITROBENZOTRIFLUORIDE AND PREPARATION OF FLUORO-NITRO-BENZOTRIFLUORIDES

[75] Inventors: David Y. Tang, E. Amherst, N.Y.; Byron R. Cotter, Northvale, N.J.; Fredrick J. Goetz, Wilmington, Del.

[73] Assignee: Occidental Chemical Corporation, Niagara Falls, N.Y.

[21] Appl. No.: 806,990

[22] Filed: Dec. 9, 1985

Related U.S. Application Data

[60] Division of Ser. No. 604,715, Apr. 27, 1984, Pat. No. 4,582,942, which is a continuation-in-part of Ser. No. 347,390, Feb. 9, 1982, Pat. No. 4,470,390.

[51] Int. Cl.$^4$ ............................................. C07C 79/12
[52] U.S. Cl. ................................... 568/937; 568/938; 570/127; 570/144
[58] Field of Search ............... 568/938, 937; 570/127, 570/144, 145

[56] References Cited

U.S. PATENT DOCUMENTS

| 4,226,811 | 10/1980 | Oeser et al. | 568/938 X |
| 4,287,374 | 9/1981 | North | 568/937 |
| 4,418,229 | 11/1983 | White | 568/937 X |
| 4,470,930 | 9/1984 | Tang et al. | 570/127 X |
| 4,590,315 | 5/1986 | Maul et al. | 570/127 |

FOREIGN PATENT DOCUMENTS 228436 11/1985 Japan .
246326 12/1985 Japan .

Primary Examiner—John F. Terapane
Assistant Examiner—Susan Wolffe
Attorney, Agent, or Firm—James F. Tao; Arthur S. Cookfair

[57] ABSTRACT

A process for the preparation of 3-chloro-4-fluoro-5-nitrobenzotrifluoride and 3,4-difluoro-5-nitrobenzotrifluoride by reaction of 3,4-di-chloro-5-nitrobenzotrifluoride and 4-chloro-3,5-dinitrobenzotrifluoride, respectively, with an alkali metal fluoride.

5 Claims, No Drawings

3,4-DIFLUORO-5-NITROBENZOTRIFLUORIDE AND PREPARATION OF FLUORO-NITRO-BENZOTRIFLUORIDES

This is a division of application Ser. No. 604,715, filed Apr. 27, 1984, now U.S. Pat. No. 4,582,942, which is a continuation-in-part of application Ser. No. 347,390, filed Feb. 9, 1982, now U.S. Pat. No. 4,470,930.

This invention relates to a vapor-phase chloro-denitration process for the preparation of nuclear-chlorinated aromatic compounds including aromatic compounds bearing both chlorine and fluorine substituents on an aromatic ring and to novel compounds prepared thereby. The chloro- and chloro-fluoro aromatic compounds prepared by the process of this invention are especially useful as chemical intermediates for a variety of useful chemical products.

The preparation of chlorobenzene compounds by chloro-denitration of the corresponding nitrobenzene compounds in the liquid phase is known. For example, the liquid phase chloro-denitration of 2-nitrobenzonitriles to form the corresponding 2-chlorobenzonitriles is disclosed in U.S. Pat. No. 4,225,534. Furthermore, it is known from the chemical literature that certain nitrobenzene or fluoronitrobenzene compounds may react with chlorine in the vapor phase with the replacement of nitro groups by chlorine atoms. (Vorozhtsov et al, Zhurnal Obshchei Khimii, Vol. 31, No. 4, pp. 1222–1226, April, 1961). Such vapor phase reactions have been shown to be feasible only with certain unsubstituted nitrobenzenes or fluoronitrobenzenes. However, it has not heretofore been known or suggested that other substituted nitrobenzenes or substituted fluoronitrobenzenes might undergo chlorodenitration by vapor phase reaction with chlorine.

Some of the dihalo and trihalo compounds that may be prepared by the process of this invention, including aromatic compounds having both chloro and fluoro substituents on the aromatic ring, have been prepared by various prior art methods. U.S. Pat. No. 4,388,472 discloses the preparation of 3,4,5-trichlorobenzotrifluoride from 2,6-dichloro-4-trifluoromethylaniline by diazotization followed by reaction with cuprous chloride in concentrated hydrochloric acid. The 3,4,5-trichlorobenzotrifluoride product may then be reacted with KF to form 3-chloro-4,5-difluorobenzotrifluoride. U.S. Pat. No. 4,259,510 discloses the preparation of trifluoromethylphenyl nitrophenylethers utilizing phenol reactants which may be prepared from substituted halobenzene reactants, including dihalobenzotrifluorides. U.S. Pat. No. 4,012,453 discloses a catalyzed oxychlorofluorination reaction of toluene, benzotrichloride, hydrogen fluoride and oxygen wherein the product includes chlorofluorobenzotrifluoride as a component. The preparation of 4-chloro-3-fluorobenzotrifluoride by diazotiation of 3-amino-4-chlorobenzotrifluoride, isolating the diazonium salt as the fluoroborate then decomposing the salt is disclosed in European Pat. No. 0 023 392 to Cartwright et al. In addition, the incidental preparation of a chlorofluorobenzotrifluoride is described in Feast et al in J. Chem. Soc. (c), 1971, 1547-49. The reference discloses 4-chloro-3-fluorobenzotrifluoride as a minor co-product obtained during the synthesis of 3,4-difluorobenzotrifluoride from 3-amino-4-fluorobenzotrifluoride.

SUMMARY OF THE INVENTION

It has now been found that substituted chloro-aromatic compounds of the formula

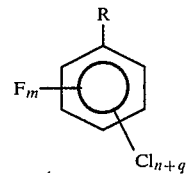

wherein m is 0, 1 or 2, n is 0, 1 or 2, q is 1 or 2, q+m+n is less than 6, and when q is 1, m is 2, R is $CF_3$; $OCF_3$, $OC_2F_5$, CN, NCO, or COCl, may be prepared by the vapor phase reaction of a chlorinating agent with a substituted nitroaromatic compound of the formula

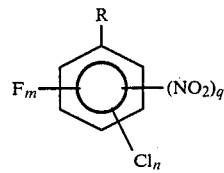

where m, n, q, and R are as defined above.

The chloro-denitration process of this invention is carried out under conditions of temperature and pressure appropriate for a vapor phase reaction, the exact conditions being dependent on the properties of the particular reactants employed. Typically, the process is carried out at atmospheric conditions and at a temperature in the range of about 200° to about 450° Celsius, or higher, preferably about 250° to 450° C. and most preferably 290° to 410° C.

The preferred chlorinating agent for economic considerations as well as efficiency of reaction, is chlorine. However, other chlorinating agents, including for example, hydrogen chloride gas, thionyl chloride, sulfuryl chloride, sulfur chloride, phosgene, phosphorus trichloride, may be employed if desired.

The proportions of reactants may vary widely with no critical limits. However, since chlorine is generally the less costly of the reactants, it is recommended to employ chlorine in excess of the amount necessary to react with the aromatic —$NO_2$ groups(s). For example, a molar ratio of $Cl_2$:$NO_2$— of about 1.1:1 to about 10:1, is preferred.

The process of the invention is useful for the preparation of various specific unfluorinated or mono- or difluorinated, mono-, di-, and tri-chloro-substituted benzotrifluorides, benzoyl chlorides, phenyl isocyanates, and benzonitriles, trifluoromethoxy-benzenes, and pentafluoroethoxybenzenes.

Typical of the chloro-substituted benzotrifluorides that may be prepared by the chloro-denitration process of this invention are 2-chlorobenzotrifluoride; 3-chlorobenzotrifluoride; 4-chlorobenzotrifluoride; 3-chloro-4-fluorobenzotrifluoride; 4-chloro-3-fluorobenzotrifluoride; 2-chloro-5-fluorobenzotrifluoride; 5-chloro-2-fluorobenzotrifluoride; 2-chloro-4-fluoro-benzotrifluoride; 4-chloro-2-fluorobenzotrifluoride; 3-chloro-5-fluorobenzotrifluoride; 2,5-dichloro-4-fluorobenzotrifluoride; 4,5-dichloro-2-fluorobenzotrifluoride; 3,5-dichloro-4-fluorobenzotrifluoride; 3,4-difluoro-5-chlorobenzotrifluoride; 2,5-difluoro-3- chlorobenzotrifluoride; 3,5-difluoro-4-chlorobenzotrifluoride; 3,4-5-trichlorobenzotrifluoride; and the like. Typical of the chloro-substituted benzoyl chlorides that may be prepared are 2-chlorobenzoyl chloride; 3-chlorobenzoyl chloride; 4-chlorobenzoyl chloride; 4-chloro-3-fluorobenzoyl chloride; 3-chloro-4-fluorobenzoyl chloride; 2-chloro-4-fluorobenzoyl chloride; 4-chloro-2-fluorobenzoyl chloride; 2-chloro-5-fluorobenzoyl chloride; 5-chloro-2-fluorobenzoyl chloride; 3-chloro-5-fluorobenzoyl chloride; 2,5-dichloro-4-fluorobenzoyl chloride; 3,5-dichloro-4-fluorobenzoyl chloride; 4,5-dichloro-2-fluorobenzoyl chloride; 3,4-difluoro-5-chlorobenzoyl chloride; 3,5-difluoro-4-chlorobenzoyl chloride; 3,4,5-trichlorobenzoyl chloride; and the like. Typical of the chloro-substituted trifluoromethoxybenzenes that may be prepared are 2-chlorotrifluoromethoxybenzene; 3-chlorotrifluoromethoxybenzene; 4-chlorotrifluoromethoxybenzene; 3-chloro-4-fluorotrifluoromethoxybenzene; 2-chloro-4-fluorotrifluoromethoxybenzene; 4-chloro-2-fluorotrifluoromethoxybenzene; 2-chloro-5-fluorotrifluoromethoxybenzene; 5-chloro-2-fluorotrifluoromethoxybenzene; 3-chloro-5-fluorotrifluoromethoxybenzene; 2,5-dichloro-4-fluorotrifluoromethoxybenzene; 4,5-dichloro-2-fluorotrifluoromethoxybenzene; 3,5-dichloro-4-fluoromethoxybenzene; 3,4-difluoro-5-chlorotrifluoromethoxybenzene; 2,5-difluoro-3-chlorotrifluoromethoxybenzene; 3,5-difluoro-4-chlorotrifluoromethoxybenzene; 3,4,5-trichloro-trifluoromethoxybenzene; and the like. Typical chloro-substituted pentafluoroethoxybenzenes that may be prepared are 2-chloro-pentafluoroethoxybenzene; 3-chloro-pentafluoroethoxybenzene; 4-chloro-pentafluoroethoxybenzene; 2-chloro-5-fluoro-pentafluoroethoxybenzene; 5-chloro-2-fluoro-pentafluoroethoxybenzene; 3-chloro-4-fluoro-pentafluoroethoxybenzene; 4-chloro-3-fluoro-pentafluoroethoxybenzene; 2-chloro-4-fluoro-pentafluoroethoxybenzene; 4-chloro-2-fluoro-pentafluoroethoxybenzene; 3-chloro-5-fluoro-pentafluoroethoxybenzene; 2,5-dichloro-4-fluoro-pentafluoroethoxybenzene; 4,5-dichloro-2-fluoro-pentafluoroethoxybenzene; 3,5-dichloro-4-fluoro-pentafluoroethoxybenzene; 3,4-difluoro-5-chloro-pentafluoroethoxybenzene; 2,5-difluoro-3-chloro-pentafluoroethoxybenzene; 3,5-difluoro-4-chloro-pentafluoroethoxybenzene; 3,4,5-trichloro-pentafluoroethoxybenzene; and the like. Typical chloro-substituted benzonitriles that may be prepared are 2-chlorobenzonitrile; 3-chlorobenzonitrile; 4-chlorobenzobenzonitrile; 2-chloro-5-fluorobenzonitrile; 5-chloro-2-fluorobenzonitrile; 3-chloro-4-fluorobenzonitrile; 4-chloro-3-fluorobenzonitrile; 2-chloro-4-fluorobenzonitrile; 4-chloro-2-fluorobenzonitrile; 3-chloro-5-fluorobenzonitrile; 2,5-dichloro-4-fluorobenzonitrile; 4,5-dichloro-2-fluorobenzonitrile; 3,5-dichloro-4-fluorobenzonitrile; 3,4-difluoro-5-chlorobenzonitrile; 2,5-difluoro-3-chlorobenzonitrile; 3,5-difluoro-4-chlorobenzonitrile; 3,4,5-trichlorobenzonitrile; and the like. Typical chloro-substituted phenyl isocyanates that may be prepared are 2-chlorophenyl isocyanate; 3-chlorophenyl isocyanate; 4-chlorophenyl isocyanate; 2-chloro-5-fluorophenyl isocyanate; 5-chloro-2-fluorophenyl isocyanate; 3-chloro-4-fluorophenyl isocyanate; 4-chloro-3-fluorophenyl isocyanate; 2-chloro-4-fluorophenyl isocyanate; 4-chloro-2-fluorophenyl isocyanate; 3-chloro-5-fluorophenyl isocyanate; 2,5-dichloro-4-fluorophenyl isocyanate; 4,5-dichloro-2-fluorophenyl isocyanate; 3,5-dichloro-4-fluorophenyl isocyanate; 3,4-difluoro-5-chlorophenyl isocyanate; 2,5-difluoro-3-chlorophenyl isocyanate; 3,5-difluoro-4-chlorophenyl isocyanate; 3,4,5-trichlorophenyl isocyanate; and the like.

The process of the invention is particularly useful for the preparation of a wide variety of specific useful chemical intermediates in substantially pure form, heretofore unavailable to the chemical industry. The chlorofluoro-aromatic compounds, prepared by the process of this invention are particularly useful for various organic syntheses based on nucleophilic substitution at the fluorine site. Thus, for example, the novel compound 5-chloro-2-fluorobenzotrifluoride may be reacted with an alkali metal hydroxide, such as potassium hydroxide, to produce 4-chloro-2-trifluoromethylphenol. Similarly, 2-chloro-4-trifluoromethylphenol, may be prepared by reaction of 3-chloro-4-fluorobenzotrifluoride with an alkali metal hydroxide, such as potassium hydroxide. Because of the higher reactivity of the nuclear fluorine, the reactants can be run under mild conditions to afford a high yield of the desired product with little or no formation of undesired isomers. The resultant chlorotrifluoromethylphenolate may be acidified to form the corresponding phenol compound. One method for the preparation of such compounds, as well as their use in the further preparation of various diphenyl ether herbicides is disclosed in detail in U.S. Pat. Nos. 4,262,152 and 4,259,510.

This novel compound 2,5-dichloro-4-fluorobenzotrifluoride may be reacted with hydroquinone, or a substituted phenol under basic conditions to form a phenyl ether of the type disclosed in U.S. Pat. No. 4,200,587 (compound V, Col. 4). As disclosed therein, such phenyl ethers may be further reacted with a suitable oxime to form useful herbicides.

The novel compound 2-chloro-5-fluorobenzotrifluoride may be similarly reacted with potassium hydroxide to produce the 4-chloro-3-trifluoromethylphenolate which may then be acidified to form the corresponding phenol compound. Upon hydrogenolyis, the 4-chloro-3-trifluoromethylphenol may be converted to 3-trifluoro-methylphenol. The use of this compound in the further preparation of pharmaceuticals is disclosed in detail in U.S. Pat. Nos. 4,168,388 and 4,018,895.

The chloro-denitration process of this invention may, in some instances, be utilized with different reactants to produce the same end product. Thus, for example, the compound 3,4,5-trichlorobenzotrifluoride, a known and useful chemical intermediate, may be prepared in accordance with this invention, by chloro-denitration of 3,4-dichloro-5-nitrobenzotrifluoride. Alternatively, 3,4,5-trichlorobenzotrifluoride may be prepared, in accordance with this invention, by chlorodenitration of 4-chloro-3,5-dinitrobenzotrifluoride. The latter compound, 4-chloro-3,5-dinitrobenzotrifluoride, is also a useful starting reactant for the preparation of a novel intermediate that may also be chloro-denitrated in accordance with this invention. Thus, for example, 4-chloro-3,5-dinitrobenzotrifluoride may be reacted with an alkali metal fluoride to form a novel intermediate, 3,4-difluoro-5-nitrobenzotrifluoride, which may in turn, be converted, by chloro-denitration in accordance with this invention, to 3-chloro-4,5-difluorobenzotrifluoride, a known and useful compound. Moreover, the reactant 3,4-dichloro-5-nitrobenzotrifluoride is also useful as a starting reactant for the preparation of a novel intermediate that may be chloro-denitrated in accordance with this invention. Thus, 3,4-dichloro-5-nitrobenzotrifluoride may be reacted with an alkali metal fluoride to form a novel intermediate, 3-chloro-4-fluoro-5-nitrobenzotrifluoride, which in turn, may be converted by chloro-denitration, in accordance with this invention, to 3,5-dichloro-4-fluorobenzotrifluoride.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

A solution of 5.3 parts of 2-nitrobenzonitrile in 37 parts of chloroform was introduced concurrently with chlorine at a $Cl_2$: nitrobenzonitrile molar ratio of 10:1 into a vapor phase reactor at a temperature of 390°–400° C. The reaction product was condensed, and collected. Analysis by gas chromatographic and mass spectrum techniques indicated 2-chlorobenzonitrile as the main product.

EXAMPLE 2

The procedure of Example 1 was repeated except that in place of 5.3 parts of 2-nitrobenzonitrile there was substituted 40 parts of 3-nitrobenzonitrile. The structure of the product 3-chlorobenzonitrile was confirmed by gas chromatography-mass spectrum and nuclear magnetic resonance analyses.

EXAMPLE 4

Chlorine and 4-nitrobenzoyl chloride (as a solution of 4.4 parts in 37 parts of carbon tetrachloride) were introduced simultaneously (at a 10:1 mol ratio of $Cl_2$: nitrobenzoyl chloride) into a vapor phase reactor maintained at a temperature of 340° to 360° C. The reaction product was condensed and collected. Analysis by gas chromatographic-mass spectrum and nuclear magnetic resonance techniques confirmed the main product as 4-chlorobenzoyl chloride.

EXAMPLE 5

The procedure of Example 4 was repeated except that 3-nitrobenzoyl chloride (5.7 parts dissolved in 1.5 parts of carbon tetrachloride) was employed in place of 4-nitrobenzoyl chloride to yield a reaction product containing 3-chlorobenzoyl chloride as the major component. The structure of the 3-chlorobenzoyl chloride product was confirmed by gas chromatographic-mass spectrum and nuclear magnetic resonance analyses.

EXAMPLE 6

Chlorine and p-nitrotrifluoromethoxybenzene (10.7 parts) were fed simultaneously at a molar ratio of 3:1, $Cl_2$: organic reactant, into a vapor phase reactor maintained at 300° to 320° C. over a 30 minute period to yield 8.2 parts of p-chlorotrifluoromethoxybenzene (83% yield). The structure of the product was confirmed by gas chromatographic-mass spectrum and $F^{19}$ nuclear magnetic resonance analysis.

EXAMPLE 7

Chlorine and 3-fluoro-2-nitrophenyl isocyanate (4.1 parts dissolved in 24 parts of carbon tetrachloride) were introduced simultaneously ($Cl_2$: organic reactant, 10:1) into a vapor phase reactor maintained at about 310° C. Analysis of the reaction product by gas chromatographic mass spectrum at $F^{19}$ nuclear magnetic resonance techniques indicated 3-fluoro-2-chlorophenyl isocyanate as the major component.

EXAMPLE 8

In a continuous process, about 14 parts per hour of 2-fluoro-5-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 20 parts of 2-fluoro-5-nitrobenzotrifluoride and about 17.3 parts of chlorine gas had been passed through the reactor. Analysis of the reaction product indicated 16.7 parts of 5-chloro-2-fluorobenzotrifluoride, a yield of 89%. The structure of the product was confirmed by gas chromatography-mass spectrum $F^{19}$ and $C^{13}$ nuclear magnetic resonance analysis.

EXAMPLE 9

14.1 parts of 5-fluoro-2-nitrobenzotrifluoride vapors and 12.1 parts of chlorine gas were passed simultaneously, over a one hour period, through a vapor-phase reactor maintained at a temperature of about 320° to 380° C. The vaporized reaction product was condensed and collected. Analysis of the reaction product indicated 12.6 parts of 2-chloro-5-fluorobenzotrifluoride, a yield of 94%. The structure of the product was confirmed by gas chromatography-mass spectrum $F^{19}$ and $C^{13}$ nuclear magnetic resonance analysis.

EXAMPLE 10

In a continuous process, about 8 parts per hour of 4-fluoro-3-nitrobenzotrifluoride vapors and about 15 parts per hour of chlorine gas were passed simultaneously through a vapor phase reactor maintained at a temperature of about 320° C. and the reaction product vapors were condensed and collected. The process was continued until about 40 parts of 4-fluoro-3-nitrobenzotrifluoride had been passed through the reactor, yielding about 36.3 parts of 3-chloro-4-fluorobenzotrifluoride product. The structure of the product was confirmed by spectral analysis.

EXAMPLE 11 (A)

About 500 parts of aqueous nitric acid was added slowly, with stirring, to a reaction vessel containing about 400 parts of 3-chloro-4-fluorobenzotrifluoride. The temperature of the reaction mixture was maintained at about 40° C. during the addition, then raised to about 60° C. and maintained thereat for about 5 hours. The reaction mixture was allowed to settle. The aqueous layer was removed and the organic layer was washed twice with 500 parts of water, treated several times with a saturated solution of sodium bicarbonate, washed with water again, dried over anhydrous magnesium sulfate, and filtered. The filtrate was distilled at reduced pressure to yield 347 parts of 5-chloro-4-fluoro-2-nitrobenzotrifluoride.

EXAMPLE 11 (B)

In a continuous process, about 14 parts per hour of 5-chloro-4-fluoro-2-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 14.7 parts of 5-chloro-4-fluoro-2-nitrobenzotrifluoride had been added and 14.7 parts of 2,5-dichloro-4-fluorobenzotrifluoride product was collected. The structure of the product was confirmed by gas chromatography-mass spectrum, $F^{19}$ and $C^{13}$ nuclear magnetic resonance analylsis.

The novel chlorofluorobenzotrifluorides of Examples 8–11 are particularly useful as intermediates for use in various organic syntheses based on nucleophilic aromatic substitution at the fluorine site. Examples 12–14 are typical of such syntheses.

EXAMPLE 12

Approximately 20 parts of 5-chloro-2-fluorobenzotrifluoride is reacted with 14 parts of powdered potassium hydroxide (85%) in dimethylsulfoxide solvent at a temperature of about 60°–70° C. for 12 to 16 hours to form 4-chloro-3-trifluoromethylphenolate. The concentrated product is mixed with ethanol solvent and reacted with hydrogen under basic conditions, in the presence of a noble metal catalyst to form m-hydroxybenzotrifluoride, a known and useful chemical intermediate.

EXAMPLE 13

Approximately 20 parts of 2-choro-5-fluorobenzotrifluoride is reacted with 14 parts of powdered potassium hydroxide (85%) in dimethylsulfoxide solvent at a temperature of about 60°–70° C. for 12 to 16 hours to form 4-chloro-3-trifluoromethylphenolate. The reaction mixture is cooled, poured into iced water, and acidified with concentrated hydrochloric acid. The aqueous mixture is then extracted with methylene chloride and the organic layer dried and concentrated to recover 4-chloro-3-trifluoromethylphenol. The concentrated product is mixed with ethanol solvent and reacted with hydrogen under basic conditions, in the presence of a nobel metal catalyst to form m-hydroxybenzotrifluoride, a known and useful chemical intermediate.

EXAMPLE 14

Approximately 20 parts of 3-chloro-4-fluorobenzotrifluoride is reacted with 14 parts of powdered potassium hydroxide (85%) in dimethylsulfoxide solvent at a temperature of about 60°–70° C. for 12 to 16 hours to form 2-chloro-4-trifluoromethylphenolate. The reaction mixture is cooled, poured into iced water, and acidified with concentrated hydrochloric acid. The aqueous mixture is then extracted with methylene chloride and the organic layer dried and concentrated to recover 2-chloro-4-trifluoromethylphenol.

EXAMPLE 15

(A) In a continuous process, about 32 parts per hour of 3,4-difluoro-5-nitrobenzotrifluoride vapors and about 30 parts per hour of chlorine gas were passed simultaneously through a vapor phase reactor maintained at a temperature of about 300° to 350° C. The vaporized reaction product was condensed and collected. The process was continued until about 9.5 parts of 3,4-difluoro-5-nitrobenzotrifluoride and about 10 parts of chlorine gas had been passed through the reactor. Analysis of the reaction product indicated 6 parts of 3-chloro-4,5-difluorobenzotrifluoride, a yield of 66%. The structure of the product was confirmed by gas chromatography-mass spectrum analysis.

(B) The 3,4-difluoro-5-nitrobenzotrifluoride starting material used in the above example was prepared as follows: a mixture of 5.4 parts of 4-chloro-3,5-dinitrobenzotrifluoride and 7.0 parts of anhydrous potassium fluoride in 10.0 parts of dimethylformamide, was heated to about 155° C. under a nitrogen atmosphere, and maintained thereat for about one hour. The reaction product was extracted with diethyl ether and dried to yield 1.74 parts of crude 3,4-difluoro-5-nitrobenzotrifluoride (38.4% yield). The structure of the product was confirmed by spectral analysis.

EXAMPLE 16

A solution of 8 parts of 4-chloro-3,5-dinitrobenzotrifluoride in 20 parts of o-chlorobenzotrifluoride was vaporized and passed through a vapor phase reactor together with 12.6 parts of chlorine gas over a half hour period. Analysis of the reaction mixture indicated the major product to be 3,4,5-trichlorobenzotrifluoride. The structure of the major product was confirmed by gas chromatography-mass spectrum analysis.

EXAMPLE 17

(A) In a continuous process about 30 parts per hour of 3-chloro-4-fluoro-5-nitrobenzotrifluoride and about 26 parts per hour of chlorine gas were passed simultaneously through a vapor phase reactor maintained at a temperature of about 300° to 350° C. The vaporized reaction product was condensed and collected until about 14.4 parts of the 3-chloro-4-fluoro-5-nitrobenzotrifluoride and about 13.7 parts of chlorine gas had been passed through the reactor. Analysis of the reaction product indicated 12.4 parts of 3,5-dichloro-4-fluorobenzotrifluoride, a yield of 90.2%. The structure of the product was confirmed by gas chromatography-mass spectrum analysis.

(B) The 3-chloro-4-fluoro-5-nitrobenzotrifluoride starting reactant employed in the above example was prepared in the follow manner. A mixture of 52 parts of 3,4-dichloro-5-nitrobenzotrifluoride, 16.2 parts of anhydrous potassium fluoride and 2.5 parts of tetramethylammonium chloride was heated and maintained at about 120° to 140° C. for about 7 hours. The mixture was then cooled to room temperature, diluted with methylene chloride, and filtered. The filtrate was distilled to yield 35.2 parts (67% yield) of 3-chloro-4-fluoro-5-nitrobenzotrifluoride. The structure of the product was confirmed by gas chromatography-mass spectrum analysis.

EXAMPLE 18

In a continuous process, about 7.5 parts of 4-fluoro-3-nitrobenzotrifluoride vapor and about 5.2 parts of hydrogen chloride gas were passed simultaneously through a vapor phase reactor maintained at a temperature of about 390° to about 420° C. over a forty minute period. The vaporized reaction product was condensed and collected. Analysis of the reaction mixture by gas chromatography indicated 3-chloro-4-fluorobenzotrifluoride as the major product.

What is claimed is:

1. 3,4-difluoro-5-nitrobenzotrifluoride.
2. A process for the preparation of 3-chloro-4-fluoro-5-nitrobenzotrifluoride which comprises reacting, 3,4-dichloro-5-nitrobenzotrifluoride with an alkali metal fluoride.
3. A process according to claim 2 wherein the alkali metal fluoride is potassium fluoride.
4. A process for the preparation of 3,4-difluoro-5-nitrobenzotrifluoride by reaction of 4-chloro-3,5-dinitrobenzotrifluoride in the liquid phase, with an alkali metal fluoride.
5. A process according to claim 4 wherein the alkali metal fluoride is potassium fluoride.

* * * * *